United States Patent [19]
Henkel

[11] Patent Number: 6,087,310
[45] Date of Patent: Jul. 11, 2000

[54] SKIN CLEANING COMPOSITIONS AND USES COMPRISING A POLYMER LATEX EMULSION

[75] Inventor: Herbert W. Henkel, East Hanover, N.J.

[73] Assignee: Castrol Limited, Swindon, United Kingdom

[21] Appl. No.: 09/158,851

[22] Filed: Sep. 23, 1998

[51] Int. Cl.[7] .................... A61K 7/50; C11D 7/50
[52] U.S. Cl. .................. 510/138; 510/130; 510/137; 510/139
[58] Field of Search ..................... 510/120, 130, 510/137, 122, 138, 139

[56] References Cited

U.S. PATENT DOCUMENTS

| | | | |
|---|---|---|---|
| 3,862,906 | 1/1975 | Chambon et al. | 252/117 |
| 4,158,543 | 6/1979 | Orlowski | 8/137 |
| 5,002,680 | 3/1991 | Schmidt et al. | 252/90 |
| 5,259,984 | 11/1993 | Hull | 252/174.17 |
| 5,538,663 | 7/1996 | Kihara et al. | 510/395 |
| 5,658,577 | 8/1997 | Fowler et al. | 424/401 |
| 5,720,961 | 2/1998 | Fowler et al. | 424/401 |
| 5,753,245 | 5/1998 | Fowler et al. | 424/401 |

FOREIGN PATENT DOCUMENTS 272099  9/1989  Germany.

OTHER PUBLICATIONS

Packaging from "Clean Hands America", Clean Hands Marketing Inc. Chatsworth, CA 91313, Made in France, probable date 1996. *NMA.

*Primary Examiner*—Necholus Ogden
*Attorney, Agent, or Firm*—McAndrews, Held & Malloy, Ltd.

[57] ABSTRACT

The present invention relates to cleaning compositions that are suitable for removing dirt, grease and oils from the hands, or other skin surfaces, without the need for additional water, or other solvent. Additionally, the cleaning compositions of this invention allow for cleaning without the need for subsequent rinsing or subsequent drying, by towel or other means. This invention also relates to methods of cleaning hands, or other skin surfaces, using the cleaning compositions of this invention.

25 Claims, No Drawings

SKIN CLEANING COMPOSITIONS AND USES COMPRISING A POLYMER LATEX EMULSION

BACKGROUND OF THE INVENTION

The present invention relates to cleaning compositions that are suitable for removing dirt, grease and oils from the hands, or other skin surfaces, without the need for additional water. Additionally, the cleaning compositions of this invention allow for cleaning without the need for subsequent rinsing or subsequent drying, by towel or other means. This invention also relates to methods of cleaning hands, or other skin surfaces, using the cleaning compositions of this invention.

East German Patent 272,099 (the '099 patent) discloses a hand cleanser that is suitable for cleaning hands soiled with oil and grease without using water and without leaving residues on the skin. This cleaner comprises from 1% to 3% (by weight) of an aqueous copolymerizate latex from styrene, 1,3-butadiene, methacrylic acid and an esterification product of Diels-Alder adducts of maleic acid. The '099 patent teaches that the successful use of a polymer latex in such a composition was surprising in that such latex mixtures are normally associated with sticky adhesives, a characteristic that is undesirable in hand cleaning compositions. Moreover, the '099 patent teaches that hand care products containing additives like alginates, 2-ethoxyethanol (carbitol), glycols, silicone compounds and ethyl alcohol, leave behind a sticky layer or they degrease the skin with simultaneous damage to the stratum corneum.

U.S. Pat. No. 3,862,906 (the '906 patent) discloses a composition for cleaning hands and other body parts comprising an aqueous emulsion of polymers or copolymers, an emulsifying agent, a fat emulsive soap and water. The disclosed compositions contain the minimum quantity of water and soap sufficient for cleaning the hands, thus making further drying unnecessary.

U.S. Pat. No. 5,002,680 (the '680 patent) discloses mild personal skin cleansers. These skin cleansers comprise a non-soap surfactant, a skin feel aid, a moisturizer, water, and a propellant, in a pressurized aerosol mousse dispenser. This mousse is disclosed to be a foam that leaves the skin feeling soft and smooth after washing. The patent discloses use of these cleansers in washing tests wherein the composition is applied, gently rubbed, then rinsed off with water.

U.S. Pat. No. 5,259,984 (the '984 patent) discloses a rinse-free cleaner composition that, after exposure to air and rubbing, extracts dirt, oil, and grease from skin or other substances, then beads up and falls off without the need for a towel. This cleaning composition comprises from 1% to 20% (by weight) of a polymer gel, a volatilizing agent, and a cleaning component comprising an alkali metal hydroxide. The polymer gel in the composition of the '984 patent is preferably an aqueous hydroxyalkylmethylcellulose-based polymeric gel; however, film-forming agents such as neoprene latex, styrene copolymer latex, polyvinyl alcohol and polyvinyl chloride latex may be employed to prepare the aqueous polymer gel component.

U.S. Pat. No. 5,538,663 discloses a detergent composition comprising polymer particles and a surface-active agent in purified water. The patent teaches various polymer class-types that are suitable for use in the composition in an amount of 0.1% to 30% by weight, and particularly 1% to 10% by weight. Of the numerous polymers disclosed, hydrophobic polymers are one class that may be utilized and styrene butadiene rubber is one such polymer disclosed. Surface active agents disclosed to be suitable for use in these compositions include ionic and non-ionic agents.

Despite the existence of the aforementioned compositions, there exists a need for a hand cleaning composition that cleans dirt, grease and oil from skin without rinsing or having to dry with a towel, that avoids the skin drying tendencies associated with solvents such as alcohols and hydrocarbons, that leaves no residue on the skin and that leaves the skin with a soothing or soft feel. Such a composition would be advantageous for its portability and convenience in situations where rinsing water (or other solvent) and toweling are either inconvenient to use or are simply unavailable.

SUMMARY OF THE INVENTION

This invention provides a cleaner composition suitable for use on skin surfaces comprising a latex emulsion of a polymer, an organosilicon compound, an emollient composition, a surfactant composition, and water. The compositions of the invention may optionally further comprise an abrasive. Upon application of these compositions to dirty hands or other skin surfaces and subsequent rubbing action, the composition will remove dirt, oil, grease and the like from the skin surface and form particles that easily fall off of the skin surface, leaving the skin surface substantially cleaned, yet also feeling smooth and soft. This invention obviates the need for additional rinsing or drying of the skin surface being cleaned. These cleaner compositions leave no residue or sticky feel on the skin and result in a soft and soothing feel to the cleaned skin surface. The compositions of the invention clean the skin without the drying tendencies associated with alcohol- or hydrocarbon solvent-containing compositions and impart a pleasant fresh scent to the cleaned skin surface.

The cleaner composition of the invention is advantageous in that it is suitable for cleaning hands without the use of rinse water or other rinsing agent. Neither rubbing nor wiping with a towel or other drying agent is necessary for effective cleaning. These properties are particularly useful to individuals in situations where access to washing facilities, rinse water, and towels or dryers is inconvenient or impossible. Examples include: home handypersons, park rangers, outdoorspersons, mechanics, and tradesmen. The cleaning compositions are portable and convenient to use, and they do not require the use of irritating ingredients sometimes found in existing cleaning compositions.

DETAILED DESCRIPTION OF THE INVENTION

This invention provides a cleaning composition, suitable for use on skin, which comprises: i) a latex emulsion of a polymer, ii) an organosilicon compound, iii) an emollient composition, iv) a surfactant composition, and v) water. Preferably, the latex emulsion is present in a higher proportion than the organosilicon compound in the cleaning compositions of this invention. In an alternate embodiment, the cleaning composition may further comprise one or more preservatives, fragrances, and/or thickeners. In another embodiment, the cleaning compositions of the invention contain an abrasive. A still further embodiment is in the form of an aerosol cleaning composition which includes a propellant, and optionally, a corrosion inhibitor. This invention also provides methods of cleaning the skin using the compositions disclosed herein.

The cleaning compositions of this invention may be in the form of a lotion, cream, aerosol, foam or mousse, or the like, and may be applied in such form.

Latex emulsions useful in this invention include those that are capable of providing cleaning action upon contact and rubbing with dirt, oil, grease and the like. Upon rubbing, the latex removes the dirt, oil, grease and grime and creates aggregates in the form of small particles, flakes, shavings and the like, that fall off of the skin, thus removing the dirt, oil grease and grime and leaving a substantially clean surface. The compositions of this invention comprise from about 20% to about 80% by weight, or alternatively from about 50% to about 70% by weight of latex emulsion.

Suitable latex emulsions comprise a polymer that is a rubber-like material. The latex emulsion may comprise a copolymer. Presently preferred latex emulsions contemplated for use in this invention include those comprising styrene butadiene copolymers. Specific latex emulsions suitable for use in this invention are exemplified by the PLIO-LITE® SBR LATEX series available from The Goodyear Tire & Rubber Company, Chemical Division, Akron, Ohio, and specifically exemplified by Goodyear product numbers LPF-6687, LPF-6733 and LPF-6758. By way of example, copolymer latex emulsions having from about 60% to about 80% butadiene monomer (based on total polymer) and about 40% to about 20% styrene monomer (based on total polymer) composition are suitable for use in this invention. Alternatively, copolymer latex emulsions having a 34/66 ratio of styrene to butadiene monomers, respectively, such as LPF-6733, are suitable for use in this invention. In many instances the latex emulsions are commercially available as proprietary preformulated packages that may also contain appropriate additives (including for example, emulsifiers (anionic and non-ionic), alkaline soaps, surfactants and the like) for maintaining the stability of the emulsion itself.

The organosilicon compounds contemplated for use in this invention are those, which are capable of enhancing the flow properties of the hand cleaner, and which function as emollients as well. This may be achieved in part by assisting in preventing undesirable stickiness or aggregation of the polymer latex. Preferably, the organosilicon compounds useful in this invention are also capable of imparting a feeling of smoothness and softness of the skin. The compositions of this invention comprise from about 1% to about 10% by weight, or alternatively from about 2% to about 6% by weight of an organosilicon compound or mixture of such compounds.

Ideally, the organosilicon compound should be inert with respect to the other ingredients in the composition and should exhibit low surface tension. Suitable organosilicon compounds have a viscosity of from about 5 to about 1000 cst at 25° C., and alternatively from about 200 to about 300 cst at 25° C. Polysiloxanes are contemplated for use, including for example, alkylpolysiloxanes, as are silicon esters, of which dimethicone copolyol lactate is one example. Commercially available organosilicon compounds, such as TBF 8-250, an alkylpolysiloxane silicone fluid available from Path Silicones, Elmwood, N.J. are suitable for use in this invention.

De-ionized water is contemplated for use in the compositions of this invention, however, water of greater purity is also suitable for use. The compositions of this invention comprise water in amounts from about 5% to about 75% by weight, or alternatively, from about 25% to about 45% by weight.

The preservatives suitable for use in the compositions of this invention are those capable of preventing or inhibiting bacterial growth in the composition during storage. The amount of preservative, which will be effective to prevent or inhibit bacterial growth, will be dependent upon on the actual identity of the preservative. A preservative suitable for skin cleaning or skin conditioning formulations is acceptable. The compositions of this invention typically comprise from about 0.10% to about 2% by weight, or alternatively from about 0.15% to about 1% by weight of a preservative.

Examples of suitable preservatives for use in this invention include: DMDH Hydantoin (5,5-dimethyl-1,3-dihydroxymethyl hydantoin), Suttocide A (sodium hydroxymethylglycinate in water), available from Sutton Laboratories (a division of International Specialty Products, Wayne, N.J.), and Surcide G-50 (gluteraldehyde), available from Surety Laboratories, Inc., Cranford, N.J.

Emollient compositions useful in the compositions of this invention comprise one or more emollients. Emollients useful in the compositions of this invention are those which impart a softer, smoother feel to the skin after application and removal of the cleaning composition. Suitable emollients are also capable of solvating water insoluble soil, dirt or grease. Generally, these include mono- and di-esters and mixtures thereof. Examples such as the hexadecyl, myristyl, isodecyl, isopropyl, octyl, or cetyl, esters of adipic, lactic, oleic, stearic, isostearic, myristic or linoleic acids as well as their corresponding alcohol esters are suitable. Esters such as isopropyl myristate, cetyl lactate, isobutyl stearate, diisopropyl adipate, dioctyl adipate and diisostearyl adipate are specifically contemplated. Such esters are preferred for use in the present invention because in addition to enhancing skin feel after use of these cleaning compositions, the ester emollients also aid in solvating and removing water insoluble dirt, grease and grime, thus facilitating the cleaning action of these compositions. The compositions of the invention comprise from about 0.1% to about 5% by weight, or alternatively from about 0.5% to about 2% by weight of an emollient composition. The compositions of the invention may comprise an adipate ester or a combination of adipate esters. Commercially available emollients such as PELEMOL 23285, which is an 80/20 blend of dioctyl adipate and diisopropyl adipate, respectively, available from Phoenix Chemical, Inc., Somerville, N.J., are suitable.

Surfactant compositions useful in the compositions of this invention comprise one or more surfactants. Surfactants useful in the compositions of this invention are those which provide an appropriate lather volume and foaming quality. Oil in water emulsifier surfactants are contemplated. The compositions of this invention comprise from about 0.1% to about 10% by weight, or alternatively from about 0.1% to about 3% by weight of a surfactant composition. Surfactants suitable for use in the compositions disclosed herein include alkoxylated alcohols, esters of sorbitan, alkanolamides or coconut alkanolamides, and the like. Among appropriate surfactant compositions are blends of ethoxylated lauryl alcohol and ethoxylated sorbitan laurate, exemplified by Lanycol 910, and coconut diethanolamides, exemplified by Naetex C. Both Lanycol 910 and Naetex C are commercially available from Lanaetex Products, Inc., Elizabeth, N.J.

Thickeners may also be used in the compositions of this invention. A thickener that provides for the desired consistency of the cleaning composition is acceptable. Polymeric thickeners are contemplated for use in the compositions of this invention. The compositions of this invention comprise from about 0.1% to about 10% by weight, or alternatively from about 0.1% to about 5% by weight of a thickener. Acrylic copolymers such as Acusol™ 820, available from Rohm and Haas Company, Philadelphia, Pa., and Structure ™3000 and Structure™3001, available from National Starch & Chemical, Bridgewater, N.J., are specifically contemplated.

Suitable fragrances useful in the compositions of this invention are any fragrance capable of imparting a pleasant fresh scent to the hands after cleaning. Suitable fragrances may also mask any unpleasant odors emanating from any other ingredient or combination of ingredients in the composition. Fragrances such as those known in the cosmetic and hand cleaner/conditioner arts are useful in this invention. The compositions of this invention may comprise from about 0.01% to about 5% by weight, or alternatively from about 0.01% to about 1% by weight of fragrance. Citrus fragrances are specifically contemplated for use in this invention.

The compositions of this invention may additionally comprise a propellant when it is desired to dispense the composition from an aerosol-type container. Propellants useful in the compositions of this invention include those materials known in the aerosol arts. Selection of a suitable propellant or propellant mixture is within the purview of one of ordinary skill in the art and may be dependant on several product attributes including for example, the choice of the valve and actuator system to be used, the desired consistency of the foam, the fill weight and gravity of the product in the aerosol, and the need to ensure adequate evacuation of the can.

The compositions of this invention may comprise from about 1% to about 20%, or alternatively from about 5% to about 10% by weight of a propellant or mixture thereof. Materials including hydrocarbons such as propane, butane, isobutane and the like, and mixtures thereof, ethers, such as dimethyl ether, and halohydrocarbons, such as hydrofluorocarbon R-134a, available from E.I. DuPont De Nemours & Co., Wilmington, Del., are contemplated for use in this invention. Other compressed gases such as carbon dioxide and nitrogen are contemplated for use. Commercially available propellants, exemplified by NP46 (73.8% n-butane and 26.2% propane), available from Phillips Chemical Company, are contemplated for use in this invention. Hydrocarbon propellants are specifically contemplated where the cleaning composition is to be applied as an aerosol.

The cleaning compositions of this invention may optionally comprise a hydrocarbon solvent, such as, for example, Isopar L, which is an aliphatic hydrocarbon available from Exxon Chemical Company, Houston, Tex. Compositions disclosed herein may comprise from about 0.1% to about 5% by weight of hydrocarbon solvent.

The cleaning compositions of this invention may also optionally comprise one or more corrosion inhibitors to prevent or inhibit corrosion of the aerosol container used to store or dispense the cleaning compositions of the invention. Such corrosion may be caused by the liquid or vapor phase, or combination thereof, of the composition. The compositions of this invention may comprise from about 0.1% to about 5% by weight, or alternatively from about 0.1% to about 2% by weight of corrosion inhibitor. Corrosion inhibitors such as alkanolamines, such as triethanol amine (TEA) and monoethanol amine (MEA), morpholine, ammonium hydroxide and sodium nitrite, or mixtures thereof, are contemplated for use in this invention.

Other appropriate additives known in the hand cleaning and conditioning formulation arts may be utilized in the compositions of this invention. These may include for example, colorants, deodorizers, dispersants, and opacifiers. Examples of these additives and other examples of the aforementioned components in the cleaning compositions of this invention are listed in McCutcheon's "Emulsifiers & Detergents—Volume 1" and "Functional Materials—Volume 2", 1997 North American Edition, Manufacturing Confectioner Publishing Co., Glen Rock, N.J., herein incorporated by reference in its entirety.

In some embodiments of this invention, a mild abrasive, such as pumice, silica, polyethylene, kaopolite (anhydrous aluminum silicate), or other such materials, may also be used. Pumice is particularly suitable for cleaning compositions of this invention that are to be applied as lotions or creams. The compositions of this invention may comprise from about 0.1% to about 10% by weight, or alternatively from about 1% to about 5% by weight of abrasive.

In one embodiment, the hand cleaning composition according to this invention comprises:
    from about 20% to about 80% by weight of a styrene butadiene latex emulsion,
    from about 1% to about 10% by weight of an organosilicon compound,
    from about 0.5% to about 5% by weight of an emollient composition,
    from about 0.1% to 10% by weight of a surfactant composition,
    from about 0.10% to about 2% by weight of a preservative composition, and
    from about 5% to about 75% by weight of water.

In an alternate embodiment, the cleaning composition directly above further comprises at least one of the following additional agents: from about 0.1% to about 5% by weight of a fragrance, from about 0.1% to about 10% by weight of a thickener or from about 0.10% to about 10% by weight of pumice.

In an alternate embodiment, the hand cleaning composition according to this invention comprises:
    from about 20% to about 80% by weight of a styrene butadiene latex emulsion,
    from about 1% to about 10% by weight of an organosilicon compound,
    from about 0.5% to about 5% by weight of an emollient composition,
    from about 0.1% to 10% by weight of a surfactant composition,
    from about 0.10% to about 10% by weight of an abrasive,
    from about 0.10% to about 2% by weight of a preservative composition, and
    from about 5% to about 75% by weight of water.

In an alternate embodiment, the cleaning composition directly above further comprises at least one of the following additional agents: from about 0.1% to about 5% by weight of a fragrance or from about 0.1% to about 10% by weight of a thickener.

In an alternate embodiment, the hand cleaning composition according to this invention comprises:
    from about 50% to about 70% by weight of a styrene butadiene latex emulsion,
    from about 2% to about 6% by weight of a dimethylpolysiloxane organosilicon compound,
    from about 0.5% to about 2% by weight of Pelemol 23285,
    from about 0.1% to about 2% by weight of Lanycol 910,
    from about 0.1% to about 2% by weight of Naetex C,
    from about 0.15% to about 1% by weight of Surcide G-50, and
    from about 25% to about 45% by weight of water.

In an alternate embodiment, the cleaning compositions described herein further comprise from about 0.10% to about 10% by weight of pumice.

In an alternate embodiment, the cleaning compositions described herein further comprise from about 0.1% to about 1% by weight of a citrus fragrance.

In an alternate embodiment, the cleaning compositions described herein further comprise from about 0.1% to about 5% by weight of a thickener such as Acusol™ 820 or Structure™ 3001.

Although the cleaning compositions of this invention are particularly suited for cleaning hands, they are useful for cleaning other skin surfaces.

In another embodiment, this invention provides cleaning compositions made by the process of combining at least a latex emulsion of a polymer, an organosilicon compound, an emollient composition, a surfactant composition, and water. Also envisioned are cleaning compositions made by the process of combining the aforementioned agents and at least one or more abrasives, preservatives, fragrances, and/or thickeners. The cleaning compositions made by the process of combining the aforementioned agents may be combined in the proportions exemplified by the various cleaning compositions disclosed throughout this specification. The agents may be added singly or multiply to one another in any order of addition during the process of combining.

In another embodiment, this invention provide a method for cleaning skin comprising:

(i) applying a cleaning composition of this invention to the skin;

(ii) rubbing said cleaning composition on the skin; and (iii) allowing the particles resulting from the interaction of the cleaning composition and any dirt, grease or grime on the skin to fall away by the rubbing action of step (ii).

This method of cleaning may utilize the cleaning compositions of this invention as a lotion, cream, aerosol, foam, mousse or combinations thereof.

In order that this invention be more fully understood, the following examples are set forth. These examples are for the purpose of illustration only and are not to be construed as limiting the scope of the invention in any way.

EXAMPLES

Equipment and Materials

The following procedures and materials were used to evaluate the performance of the hand-cleaning compositions of this invention. Examples A–D, I–J and N–O exemplify cleaning compositions of this invention. Examples E–H and K–M exemplify currently available cleaning compositions that are evaluated for comparative purposes.

Examples A–D, I–J and N–O are cleaning compositions prepared in the proportions as listed in Table 1. Examples E–H and K–M are sample cleaning compositions that are commercially available. They are individually described below.

Example E

Water, Pumice, d-Limonene, Nonionic Surfactant, Corn Huskers Lotion (Water, Glycerin, SD Alcohol, Algin, Tea-Oleoyl Sarcosinate, Methylparaben, Guar Gum, Calcium Sulfate, Calcium Chloride, Tea-Fumarate, Tea-Borate, Fragrance), Triethanolamine, Carbomer, Lanolin, Methylchloroisothiazolinone, Methylisothiazolinone, Vitamin E, Aloe Vera, Jojoba Oil.

Example F

Water, Pumice, d-Limonene, Vegetable Oil or Dipentene, Linear Alcohol Alkoxylate, Aloe Extract, Baby oil, Carbomer, Jojoba Oil, Lanolin Oil, Methylchloroisothiazolinone, Methylisothiazolinone, Tocopheryl Acetate, Triethanolamine.

Example G

Paraffinic Solvent, Water, Mineral Oil, Tallates, Surfactant, Propylene Glycol, Petrolatum, Allantoin, Aloe Extract, Inositol, Lanolin, Methionine, Preservative, Vitamins A B C E H, Wheat Germ Extract.

Example H

Water, d-Limonene, Propylene glycol, Castor Oil, Nonionic Surfactant, Corn Huskers Lotion, Triethanolamine, Magnesium Aluminum Silicate, Carbomer, Lanolin, Preservative, Vitamin E, Aloe Vera, Jojoba Oil.

Example K

Water, Pumice, d-Limonene, Nonionic Surfactant, Corn Huskers Lotion (Water, Glycerin, SD Alcohol, Algin, Tea-Oleoyl Sarcosinate, Methylparaben, Guar Gum, Calcium Sulfate, Calcium Chloride, Tea-Fumarate, Tea-Borate, Fragrance), Triethanolamine, Carbomer, Lanolin, Methylchloroisothiazolinone, Methylisothiazolinone, Vitamin E, Aloe Vera, Jojoba Oil.

Example L

Water, Pumice, d-Limonene, Vegetable Oil or Dipentene, Linear Alcohol Alkoxylate, Aloe Extract, Baby oil,

TABLE 1

Composition of Examples
(% of total composition by weight)

| Component | Ex. A | Ex. B | Ex. C | Ex. D | Ex. I | Ex. J | Ex. N | Ex. O |
|---|---|---|---|---|---|---|---|---|
| Latex SBR 6733 | 58.00 | 58.00 | 58.50 | 60.00 | 57.00 | 57.00 | 57.00 | 57.00 |
| Silicon TBF 8-250 | 4.00 | 4.00 | 4.00 | 4.00 | 4.00 | 3.80 | 3.80 | 3.80 |
| DI Water | 32.60 | 30.60 | 31.60 | 33.40 | 31.70 | 34.00 | 31.20 | 30.80 |
| Surcide G-50 | 0.10 | 0.10 | 0.10 | 0.10 | 0.30 | 0.30 | 0.20 | 0.20 |
| Structure ™ 3001 | 1.00 | 1.00 | 1.00 | — | 1.30 | — | — | — |
| Acusol 820 | — | — | — | — | — | 1.10 | 1.00 | 1.10 |
| Naetex C | 0.30 | 0.30 | 0.30 | — | 0.30 | 0.30 | 0.30 | 0.30 |
| PELEMOL 23285 | 1.00 | 1.00 | 1.00 | 1.00 | 1.00 | 1.00 | 1.00 | 1.00 |
| Isopar L | 1.50 | 1.50 | — | — | — | — | — | — |
| Lanycol 910 | 1.00 | 1.00 | 1.00 | 1.00 | 1.20 | 2.00 | 2.00 | 2.00 |
| Fragrance | 0.50 | 0.50 | 0.50 | 0.50 | 0.50 | 0.50 | 0.50 | 0.50 |
| Pumice 1 | — | — | — | — | 2.70 | — | 3.00 | 3.00 |
| Pumice O ½ | — | 2.00 | 2.00 | — | — | — | — | — |

Carbomer, Jojoba Oil, Lanolin Oil, Methylchloroisothiazolinone, Methylisothiazolinone, Tocopheryl Acetate, Triethanolamine.

Example M

C12–C16 Isoparaffin, Water, Mineral oil, Sodium oleate, Pumice, Trideceth—9 Propylene glycol, Petrolatum, Ethanolamine, Allantoin, Aloe Extract, Ascorbic acid, Biotin, Lanolin, Methionine, Pantothenic acid, Refinol, Tocopheryl acetate, Zinc Pyrithione, Blue #1, Yellow #5.

The tests were conducted using a test "Urban soil", similar to ASTM D4488. This "Urban soil" was a combination of the following ingredients in the stated proportions:

| Sanders-Lambert Synthetic Urban Soil | |
|---|---|
| Ingredient | Weight (g) |
| Hyperhumus | 38.0 |
| Portland cement | 15.0 |
| Low color furnace carbon black | 1.5 |
| Synthetic red iron oxide | 0.3 |
| Powdered silica (200–300 mesh) | 15.0 |
| Bandy black clay | 16.7 |
| Stearic acid | 1.5 |
| Oleic acid | 1.5 |
| Palm oil | 3.0 |
| Cholesterol | 1.0 |
| Vegetable oil (iodine value of 110±10) | 1.0 |
| n-octadecane (tech. grade) | 1.0 |
| 1-octadecene (tech. grade) | 1.0 |
| linoleic acid (tech. grade) | 2.0 |
| white mineral oil | 1.5 |

Hyperhumus from Hyperhumus Co., Newton NJ
Carbon black from Cities Service Co., Raven 410 powder or equal
Iron oxide from Cities Service Co., Mapico Red 387 or equal
Clay from Spinks Clay Co., Newport KY The ingredients are mixed in a ball mill with 150 mL of distilled water and about 210 9.5-mm. diameter grinding media steel balls and ground for 24 hours. The mixture is air dried overnight, ground in a mortar and passed through a 100-mesh screen.

Test Procedure

The test was conducted with a panel of ten people. Both the panelists and a moderator rated the cleaning of each test according to a 10 point scale, where 0=no soil removal and 10=100% soil removal. The order of the cleaners and the soil application was randomized for each panelist. Examples A–H were examined using one panel, designated herein as "Panel A". Examples I–M were examined using a second panel, designated herein as "Panel B".

Soil Application

The amount of soil applied was different for each soil. The amount of soil should be enough to sufficiently challenge the cleaners and still allow for differentiation between them. Soil and amounts used were:

Urban Soil—Sanders-Lambert soil mixed 1:1 with mineral oil (25 g)
Valvoline grease with clay (0.5 g)
Mineral Oil
Dirty motor oil
Shoe polish, Kiwi black
Oil paint (Rustoleum Outdoor Decor 7777 satin black)
Ball point ink/Permanent marker
Carbon black
Wood stain, Red Devil
Wood putty, Minwax
Used diesel oil Each panelist put an unpowdered latex glove on one hand. The soil was weighed onto weighing paper or waxed paper and applied directly to the bare hand. The moderator or panelist rubbed the hand to distribute the soil as evenly as possible over the hand, palm side only.

Cleaning

Two minutes after the soil was applied, the hands were cleaned with 1 g of the respective cleaner for a period of one minute. Samples of the Example F and Example G compositions were used with a few drops of water, all other samples were used without additional water. The soil removal was then evaluated on a scale of 1 to 10, with 10 being 100% soil removal. The results are summarized in Tables 2–11. The cleaning rating is an average of the combined responses of each of the 10 panelists and the moderator for each test sample. As can be seen from Tables 2–11, panelists rated the compositions of this invention (samples from Examples A–D and I–J) as having superior cleaning ability as compared to commercially available compositions (samples from Examples E–H and K–M, respectively).

TABLE 2

Rating of Cleaning Ability
Against Sanders-Lambert Urban Soil/Mineral Oil

| TEST SAMPLE | RATING (Std. Dev.) |
|---|---|
| Panel A | |
| Example A | 8.6 (0.958) |
| Example B | 7.7 (1.379) |
| Example C | 7.9 (0.841) |
| Example D | 9.1 (0.686) |
| Example E | 6.3 (1.720) |
| Example F | 6.4 (1.930) |
| Example G | 7.0 (1.743) |
| Example H | 5.9 (1.836) |
| Panel B | |
| Example I | 8.1 (1.255) |
| Example J | 7.9 (1.280) |
| Example K | 7.5 (0.857) |
| Example L | 6.9 (0.985) |
| Example M | 8.1 (0.981) |

TABLE 3

Rating of Cleaning Ability
Against Grease

| TEST SAMPLE | RATING (Std. Dev.) |
|---|---|
| Panel A | |
| Example A | 10.0 (0.112) |
| Example B | 9.7 (0.591) |
| Example C | 9.8 (0.377) |
| Example D | 9.9 (0.393) |
| Example E | 9.3 (1.164) |
| Example F | 9.8 (0.734) |
| Example G | 9.8 (0.380) |
| Example H | 9.6 (0.483) |

TABLE 3-continued

Rating of Cleaning Ability
Against Grease

| TEST SAMPLE | RATING (Std. Dev.) |
|---|---|
| Panel B | |
| Example I | 9.1 (1.134) |
| Example J | 8.9 (1.415) |
| Example K | 9.7 (0.401) |
| Example L | 9.8 (0.343) |
| Example M | 9.7 (0.343) |

TABLE 4

Rating of Cleaning Ability
Against Dirty Motor Oil

| TEST SAMPLE | RATING (Std. Dev.) |
|---|---|
| Panel A | |
| Example A | 10.0 (0.112) |
| Example B | 9.6 (0.467) |
| Example C | 9.7 (0.564) |
| Example D | 9.7 (0.462) |
| Example E | 10.0 (0.224) |
| Example F | 9.2 (1.196) |
| Example G | 10.0 (0.000) |
| Example H | 9.2 (1.322) |
| Panel B | |
| Example I | 9.7 (0.401) |
| Example J | 9.7 (0.377) |
| Example K | 9.9 (0.275) |
| Example L | 9.8 (0.373) |
| Example M | 9.9 (0.262) |

TABLE 5

Rating of Cleaning Ability
Against Shoe Polish

| TEST SAMPLE | RATING (Std. Dev.) |
|---|---|
| Panel A | |
| Example A | 6.1 (1.210) |
| Example B | 7.3 (1.418) |
| Example C | 6.9 (1.314) |
| Example D | 7.6 (1.245) |
| Example E | 6.4 (2.073) |
| Example F | 8.5 (1.118) |
| Example G | 9.0 (0.809) |
| Example H | 6.5 (1.100) |
| Panel B | |
| Example I | 6.1 (1.849) |
| Example J | 6.5 (1.716) |
| Example K | 9.2 (0.780) |
| Example L | 9.2 (0.413) |
| Example M | 9.5 (0.380) |

TABLE 6

Rating of Cleaning Ability
Against Putty

| TEST SAMPLE | RATING (Std. Dev.) |
|---|---|
| Panel A | |
| Example A | 8.5 (1.118) |
| Example B | 8.8 (2.148) |
| Example C | 9.0 (0.843) |
| Example D | 9.4 (0.981) |
| Example E | 6.3 (2.912) |
| Example F | 8.8 (1.444) |
| Example G | 9.5 (0.850) |
| Example H | 6.3 (2.546) |
| Panel B | |
| Example I | 9.1 (1.029) |
| Example J | 9.3 (0.715) |
| Example K | 9.0 (1.164) |
| Example L | 9.1 (1.971) |
| Example M | 9.4 (1.122) |

TABLE 7

Rating of Cleaning Ability
Against Used Diesel Oil

| TEST SAMPLE | RATING (Std. Dev.) |
|---|---|
| Panel A | |
| Example A | 9.6 (0.793) |
| Example B | 9.0 (1.577) |
| Example C | 9.9 (0.286) |
| Example D | 9.5 (0.678) |
| Example E | 9.5 (0.819) |
| Example F | 9.6 (0.667) |
| Example G | 9.8 (0.373) |
| Example H | 9.5 (0.647) |
| Panel B | |
| Example I | 9.1 (1.119) |
| Example J | 8.4 (1.975) |
| Example K | 8.7 (1.523) |
| Example L | 9.3 (0.786) |
| Example M | 9.5 (0.538) |

TABLE 8

Rating of Cleaning Ability
Against Oil Paint

| TEST SAMPLE | RATING (Std. Dev.) |
|---|---|
| Panel A | |
| Example A | 1.5 (1.235) |
| Example B | 1.5 (1.094) |
| Example C | 2.3 (1.372) |
| Example D | 2.5 (1.997) |
| Example E | 6.8 (1.361) |
| Example F | 5.9 (1.623) |
| Example G | 7.1 (1.685) |
| Example H | 5.1 (1.510) |
| Panel B | |
| Example I | 1.3 (0.444) |
| Example J | 2.1 (1.205) |
| Example K | 7.4 (1.134) |
| Example L | 7.2 (1.415) |
| Example M | 7.6 (0.837) |

TABLE 9

Rating of Cleaning Ability  
Against Ink and a Marker

| TEST SAMPLE | RATING (Std. Dev.) |
|---|---|
| Panel A | |
| Example A | 6.0 (1.716) |
| Example B | 6.1 (2.719) |
| Example C | 6.7 (2.296) |
| Example D | 7.5 (1.669) |
| Example E | 9.7 (0.472) |
| Example F | 9.8 (0.294) |
| Example G | 6.3 (1.534) |
| Example H | 8.7 (1.839) |
| Panel B | |
| Example I | 5.8 (2.167) |
| Example J | 4.8 (2.308) |
| Example K | 9.3 (0.639) |
| Example L | 9.2 (0.696) |
| Example M | 8.4 (1.268) |

TABLE 10

Rating of Cleaning Ability  
Against Carbon Black

| TEST SAMPLE | RATING (Std. Dev.) |
|---|---|
| Panel A | |
| Example A | 7.7 (0.924) |
| Example B | 8.3 (1.032) |
| Example C | 8.3 (1.218) |
| Example D | 8.6 (0.872) |
| Example E | 4.7 (1.920) |
| Example F | 4.9 (1.832) |
| Example G | 6.6 (1.603) |
| Example H | 4.8 (1.908) |
| Panel B | |
| Example I | 7.7 (0.835) |
| Example J | 8.1 (0.754) |
| Example K | 5.5 (1.885) |
| Example L | 5.9 (1.134) |
| Example M | 5.8 (1.240) |

TABLE 11

Rating of Cleaning Ability  
Against Wood Stain

| TEST SAMPLE | RATING (Std. Dev.) |
|---|---|
| Panel A | |
| Example A | 2.8 (2.074) |
| Example B | 3.3 (2.105) |
| Example C | 4.1 (2.164) |
| Example D | 2.8 (1.830) |
| Example E | 7.3 (2.111) |
| Example F | 8.1 (1.234) |
| Example G | 8.1 (1.711) |
| Example H | 6.0 (2.454) |
| Panel B | |
| Example I | 7.3 (0.865) |
| Example J | 7.3 (1.550) |
| Example K | 8.9 (0.805) |
| Example L | 9.1 (0.788) |
| Example M | 9.1 (0.936) |

While we have described a number of embodiments of this invention, it is apparent that our basic compositions may be altered to provide other embodiments that do not depart from the basic teachings disclosed herein. Therefore, it will be appreciated that one of skill in the art may recognize that modifications may be made to the embodiments specifically disclosed in this application, yet these modifications are within the scope and spirit of the invention as set forth in the appended claims.

We claim:

1. A composition suitable for cleaning skin, comprising from about 50% to about 80% by weight of a polymer latex emulsion, an organosilicon compound, an emollient, a surfactant, and water.

2. The cleaning composition according to claim 1, further comprising an abrasive.

3. The cleaning composition according to claim 2, wherein the abrasive is pumice.

4. The cleaning composition according to claim 1, further comprising at least one component selected from the group consisting of: preservatives, fragrances and thickeners.

5. The cleaning composition according to claim 1, wherein the cleaning composition is a lotion, cream, aerosol, foam or mousse.

6. The cleaning composition according to claim 1, further comprising a propellant.

7. The cleaning composition according to claim 6, wherein the propellant is a hydrocarbon propellant.

8. The cleaning composition according to claim 6, further comprising a corrosion inhibitor.

9. The cleaning composition according to claim 6, comprising from about 1% to about 20% by weight of the propellant.

10. The cleaning composition according to claim 1, wherein the emulsion of a rubber-like polymer is present in a higher proportion by weight than said organosilicon compound.

11. The cleaning composition according to claim 1, wherein the emulsion of a rubber-like polymer is a styrene butadiene latex emulsion.

12. The cleaning composition according to claim 1, wherein the organosilicon compound is an alkylpolysiloxane.

13. The cleaning composition according to claim 12, wherein the organosilicon compound is a dimethylpolysiloxane silicone fluid.

14. The cleaning composition according to claim 1, wherein said emollient comprises a mono- or di-ester, or mixture thereof.

15. The cleaning composition according to claim 1, wherein said emollient comprises an adipate ester or combination of adipate esters.

16. The cleaning composition according to claim 1, wherein said emollient comprises dioctyl adipate and diisopropyl adipate.

17. The cleaning composition according to claim 1, wherein the surfactant is selected from the group consisting of alkoxylated alcohols, esters of sorbitan, alkanolamides, and mixtures thereof.

18. A cleaning composition according to claim 1, wherein the surfactant is selected from the group consisting of ethoxylated lauryl alcohol, ethoxylated sorbitan laurate, coconut diethanolamide, and mixtures thereof.

19. A cleaning composition according to claim 1, comprising:

from about 50% to about 80% by weight of a polymer latex emulsion, from about 1% to about 10% by weight of an organosilicon compound, from about 0.5% to about 5% by weight of an emollient, from about 0.1% to about 10% by weight of a surfactant, and from about 5% to about 45% by weight of water.

20. The cleaning composition according to claim 19, further comprising from about 0.1% to about 10% by weight of pumice.

21. The cleaning composition according to claim 19, further comprising from about 0.1% to about 2% by weight of a preservative.

22. A cleaning composition according to claim 19, comprising:

from about 50% to about 70% by weight of a styrene butadiene latex emulsion, from about 2% to about 6% by weight of a dimethylpolysiloxane silicone fluid, from about 25% to about 45% by weight of water, from about 0.15% to about 1% by weight of a preservative, from about 0.5% to about 2% by weight of an adipate ester, from about 0.1% to about 3% by weight of a surfactant selected from the group consisting of ethoxylated lauryl alcohol, ethoxylated sorbitan laurate, and mixtures thereof, and from about 0.1% to about 3% by weight of a coconut diethanolamide.

23. The cleaning composition according to claim 22, further comprising from about 1% to about 5% by weight of pumice.

24. A method for cleaning skin comprising the steps of:

(i) applying a cleaning composition comprising from about 50% to about 80% by weight of a polymer latex emulsion, an organosilicon compound, an emollient, a surfactant, and water, to the skin;

(ii) rubbing said cleaning composition on the skin to form particles; and (iii) allowing the particles to fall away by means of further rubbing action.

25. A composition suitable for cleaning skin made by combining from about 50% to about 80% by weight of a polymer latex emulsion, from about 1% to about 10% by weight of an organosilicon compound, from about 0.5% to about 5% by weight of an emollient, from about 0.1% to about 10% by weight of a surfactant, and from about 5% to about 45% by weight of water.

* * * * *